(12) United States Patent
Kim

(10) Patent No.: US 10,610,001 B2
(45) Date of Patent: Apr. 7, 2020

(54) MASK DEVICE FOR FACIAL SKIN CARE

(71) Applicant: Jong-Chen Kim, Bucheon-si (KR)

(72) Inventor: Jong-Chen Kim, Bucheon-si (KR)

(*) Notice: Subject to any disclaimer, the term of this patent is extended or adjusted under 35 U.S.C. 154(b) by 72 days.

(21) Appl. No.: 15/621,748

(22) Filed: Jun. 13, 2017

(65) Prior Publication Data

US 2018/0352936 A1 Dec. 13, 2018

(51) Int. Cl.
*A61N 5/06* (2006.01)
*A45D 44/00* (2006.01)

(52) U.S. Cl.
CPC .......... *A45D 44/002* (2013.01); *A61N 5/0616* (2013.01); *A45D 2200/205* (2013.01); *A61N 2005/0626* (2013.01); *A61N 2005/0647* (2013.01); *A61N 2005/0652* (2013.01); *A61N 2005/0659* (2013.01); *A61N 2005/0663* (2013.01)

(58) Field of Classification Search
CPC ................ A45D 44/002; A61N 5/0616; A61N 2005/0647
See application file for complete search history.

(56) References Cited

U.S. PATENT DOCUMENTS

| | | | | |
|---|---|---|---|---|
| 4,185,329 A * | 1/1980 | Sarazen | ................... | A61F 9/061 2/428 |
| 8,336,114 B1 * | 12/2012 | Lee | ........................ | A42B 3/145 2/9 |
| 2004/0153131 A1 * | 8/2004 | Yorke | ................... | A61N 5/0617 607/91 |
| 2005/0070977 A1 * | 3/2005 | Molina | ................... | A61N 2/002 607/88 |
| 2006/0030908 A1 * | 2/2006 | Powell | ................. | A61N 5/0616 607/88 |
| 2006/0268220 A1 * | 11/2006 | Hogan | .................... | A61F 9/025 351/47 |
| 2010/0076529 A1 * | 3/2010 | Tucker | ................. | A61N 5/0616 607/90 |
| 2011/0015707 A1 * | 1/2011 | Tucker | ................. | A61N 5/0616 607/90 |

(Continued)

FOREIGN PATENT DOCUMENTS

KR 20070005491 A * 1/2007
KR 1020070005491 1/2007

(Continued)

*Primary Examiner* — Michael W Kahelin
*Assistant Examiner* — Sana Sahand
(74) *Attorney, Agent, or Firm* — IPLA P.A.; James E. Bame

(57) ABSTRACT

A mask device for facial skin care includes: an outer mask, which is formed to be spaced apart from a user's face at a predetermined interval, has a size to cover the whole face, and includes first and second eye protection holes located around the eyes and slots respectively formed at a left end portion and a right end portion; an LED module, and to which a control line receiving electric power connected to the controller of the outside and a control signal is connected; an inner mask, which is located outside the LED module, has a size to cover the hole face; and an eye protection member whose one end is combined to the first and second eye protection holes of the inner mask and the other end protrudes to come into contact with the user's eyes.

11 Claims, 15 Drawing Sheets

(56) References Cited

U.S. PATENT DOCUMENTS

| | | | |
|---|---|---|---|
| 2014/0316492 A1* | 10/2014 | Min | A61N 5/0613 |
| | | | 607/91 |
| 2014/0350643 A1* | 11/2014 | Pepitone | A61N 5/0616 |
| | | | 607/89 |
| 2016/0056653 A1* | 2/2016 | Tapper | H02J 7/0052 |
| | | | 607/91 |
| 2018/0178034 A1* | 6/2018 | Iguchi | A61N 5/0616 |
| 2018/0221682 A1* | 8/2018 | Pepitone | A61N 5/0617 |

FOREIGN PATENT DOCUMENTS

| | | | |
|---|---|---|---|
| KR | 20110100122 A | * | 9/2011 |
| KR | 1020110100122 | | 9/2011 |
| KR | 1020130130489 | | 12/2013 |
| KR | 101497617 | | 3/2015 |
| KR | 101497617 B1 | * | 3/2015 |

* cited by examiner

FIG. 8

| working time | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| Therapy | pimple | | | | | | | | | | IR | | | | | | | | | IR | IR |
| | scar | | | | | | | | | | | | | | | | | | | | |
| | atopy | | | | IR | IR | | | | IR | IR | | | IR | IR | | | | IR | IR | IR |
| | psoriasis | | | IR | IR | | | | IR | IR | IR | | | | | | | IR | | | |
| | injuries | | | IR | | | | | | | | | | | | | | | | | |
| Healing | relaxing effect | | | | | | | | | | | | | | | | | | | | |
| | prevention of infection | | | | | IR | IR | IR | IR | IR | | | | | IR | IR | | | | | IR |
| | skin refreshing | | | | | | | | | | | | | | | | | | | | |
| | pain relief | | | | IR | IR | IR | IR | IR | IR | IR | | IR | IR | IR | IR | IR | IR | IR | IR | IR |
| Tightening | wrinkle treatment | | | | | | | | | | | | IR | | | | | | | | |
| | prevention of hair loss | | | IR | IR | IR | IR | IR | IR | IR | IR | IR | IR | IR | IR | IR | | | IR | IR | IR |
| | cellulite treatment | | | | | IR | | | IR | IR | IR | | IR | | IR | | | | | | |
| | promotion of blood circulation | | | | | | | | | | | | | | | | | | | | |
| Beauty | sedation of skin troubles | | | | | | | | | | | | | | | | | | | | |
| | resistance to ultraviolet rays | | | | | | | | | | | | | IR | IR | IR | | IR | | IR | IR |
| | generation of collagen | | | | | | | | | | | | | IR | | | | | IR | | |
| | inhibition of sebum | IR | IR | | | | | | | | | IR | | | | | | | IR | | | violet color ○    green color ○    navy color ○    red color ○    orange color ○    yellow color ○

MASK DEVICE FOR FACIAL SKIN CARE

BACKGROUND

The present invention relates to a mask device for facial skin care, and more particularly, to a mask device for facial skin care, which can relieve facial skin troubles of various kinds using RGB LED lights and IR LED lights, protect the sight of eyes, and relieve the pressure applied to the eyes even though a user wears it for a long time.

In general, color therapy is used for the purpose of skin care using influences of color energies and wavelengths of lights of the energies on the human body.

For the color therapy, LEDs are used for expressing lights of colors. For instance, it is known that a red LED (R LED) having the wavelength of about 660 nm is effective in skin elasticity, blood circulation, an increase of metabolism of subcutaneous tissues and fats, and so on. It is also known that a blue LED (B LED) having the wavelength of about 445 nm has effects for a pimpled face and a dry skin. It is also known that a green LED (G LED) having the wavelength of about 530 nm is effective in strengthening functions of cell layers and preventing aging. Such R, G and B LEDs have been used for the purpose of skin care.

Skin care devices using such LEDs having specific wavelengths have been mainly used at beauty shops or skin care shops. Such skin care devices is generally divided into a skin care device of a stand type lighting tower having an LED with a specific wavelength stored in a lighting unit and a portable skin care device that allows a user to directly rub face skin with the portable skin care device to which LEDs for ion massage and color therapy are combined.

The former skin care device just has an effect of exhibition and is not suitable for skin care because a distance from the LEDS of the specific LEDs to the user's face skin is too long and probability that such specific wavelengths have an influence on a spotty skin is very low. Moreover, the latter skin care device is very suitable for skin care because it does skin care using the specific wavelengths of the lights of the LEDs while the user rubs the face skin by the surface of the ion massage device, but is complicated in that the user has to directly rub the face skin while holding the massage device with one hand.

So, Korean Patent Laid-open No. 10-2011-0100122 discloses a 'mask for skin care' which radiates wavelengths of LEDs to a user's face when the user wears the mask on his or her face.

However, the mask for skin care disclosed in Korean Patent Laid-open No. 10-2011-0100122 has another disadvantage in that it may have a bad influence on the user's eyesight because lights of the LEDs directly get in contact with the user's eyes if the user moves.

SUMMARY OF THE INVENTION

Accordingly, the present invention has been made in view of the above-mentioned problems occurring in the prior art, and it is an object of the present invention to provide a mask device for facial skin care, which can relieve facial skin troubles of various kinds using RGB LED lights and IR LED lights, protect the sight of eyes, and relieve the pressure applied to the eyes even though a user wears it for a long time.

It is another object of the present invention to provide a mask device for facial skin care, which has LEDs formed integrally, thereby providing LEDs more than the conventional skin care devices having LEDs formed individually.

It is a further object of the present invention to provide a mask device for facial skin care, which provides different skin care menus so that a user can select working zones of the mask device for facial skin care.

To accomplish the above object, according to the present invention, there is provided a mask device for facial skin care, which includes a mask generating RGB lights and IR lights, and a controller for providing the mask with electric power and optical control signals. The mask includes: an outer mask, which is formed to be spaced apart from a user's face at a predetermined interval, has a size to cover the whole face, and includes first and second eye protection holes located around the eyes and slots respectively formed at a left end portion and a right end portion; an LED module, which is located on the inner face of the outer mask and includes a plurality of RGB LEDs for generating RGB colors and a plurality of IR LEDs for generating infrared rays, and to which a control line receiving electric power connected to the controller of the outside and a control signal is connected; an inner mask, which is located outside the LED module, has a size to cover the hole face, is combined to the outer mask, includes LED through holes formed corresponding to the LEDs so that lights generated from the RGB LEDs and the IR LEDs of the LED module face toward the user's face, is formed opaquely to block penetration of lights through any other portions but the LED through holes, and includes first and second eye protection holes formed to correspond to the first and second eye protection holes of the outer mask and slots respectively formed at the left end portion and the right end portion; an eye protection member whose one end is combined to the first and second eye protection holes of the inner mask and the other end protrudes to come into contact with the user's eyes; light diffusion members of a convex form respectively disposed on the RGB LEDs and the IR LEDs to diffuse emitted lights; and a wearing member fixed to combine the outer mask and the inner mask with each other and worn on the user's head. The wearing member includes: fixing blocks fixed at both sides of the outer mask and the inner mask; a forehead holder rotatably fixed on the fixing block and supported on the user's forehead; an occipital region holder disposed on the forehead holder to be supported on the user's occipital region; and fastening members which penetrate the fixing blocks, the forehead holder, the slots of the outer mask, and the slots of the inner mask to fix the fixing blocks to the outer mask and the inner mask and support rotation of the forehead holder. The inner mask has a stepped portion, which has a bracket and is formed at an edge portion so that the inside part on which the LED module is located is spaced apart from the outer mask at a predetermined interval. An LED module interval control member is movably supported on the bracket to pull the LED module so that the LED module gets in contact with the inner mask, or to push the LED module so that the LED module is spaced apart from the inner mask.

Preferably, an arm type protrusion is formed to protrude between the first and second eye protection holes to fix the position of the eye protection member, and stepped jaws are respectively formed on the outer circumferential surfaces of the LED through holes of the inner mask to surround and support the LEDs of the LED module. The eye protection member includes: first and second protection tubes which are in a cylindrical form and of which end portions are respectively combined to the first eye protection hole and the second eye protection hole; a connector of which one end and the other end are respectively combined to the first and second protection tubes; a fixing rod which extends from the central lower portion of the connector and is combined to the arm type protrusion of the inner mask; a nose support which extends from the fixing rod to be put on the user's bridge of the nose; insertion grooves respectively formed in the outer faces of the first and second protection tubes; and protection covers respectively combined to the insertion grooves while surrounding the first and second protection tubes. Stoppers are respectively formed on the first and second protection tubes inserted into the inner mask to protrude outwardly in order to prevent the first and second protection tubes from being separated from the first and second eye protection holes after the ends of the first and second protection tubes are respectively inserted into the first and second eye protection holes.

Preferably, the fixing block includes: an outer block located at the outer mask; an inner block located at the inner mask to be combined to the outer block; and a support block combined to the inner block to support the forehead holder. The outer block has a plurality of outer fastening portions to which the fastening member is combined, the inner block has a plurality fastening holes, which correspond to the outer fastening portions and through which the fastening member penetrates, and a plurality of inner fastening portions corresponding to the support block, and the support block has a plurality of fastening holes which correspond to the inner fastening portions and through which the fastening members penetrate. A plurality of fastening members are combined to the outer fastening portions inserted into the slots after passing through the fastening holes so as to be fixed while pressurizing the outer block and the inner block to the outer mask and the inner mask, is combined to the inner fastening portions after passing through the forehead holder while penetrating the fastening holes, such that the inner block and the support block are combined and the forehead holder is fixed to be able to rotate.

Preferably, the slots are elongated holes, the outer fastening portions are formed in a rectangular shape to correspond to the slots, and the fastening members are bolts, and the outer fastening portions and the inner fastening portions respectively have screw taps with which the bolts of the fastening members are screw-coupled.

Preferably, the forehead holder is made with a flexible plate which is bent in the form of an arc, and both ends of the forehead holder are fixed to the fixing block. The occipital region holders are bands respectively fixed to both ends of the forehead holder.

Preferably, the forehead holder has projections, which are formed to project downwardly form both sides there, and which are rotatably fixed to the fixing block when the fastening members penetrate therethrough.

Preferably, the bracket has a yoke transformed elastically, and the LED module interval control member includes: a shaft whose one end is fixed to the LED module and the other end protrudes outwardly after penetrating the inner mask and which is guided through the yoke of the bracket; and a fixing protrusion which is formed on the shaft and is movably caught and fixed to the yoke of the bracket.

Preferably, the shaft has a male screw thread formed on the outer circumferential surface of an end thereof, and the LED module has a wing piece having a screw tap corresponding to the male screw thread of the shaft.

Preferably, the controller includes: a control line a control line connecting unit to which the control line of the mask is connected; a display unit for displaying information of various menus; and a control member 240 for controlling information of various kinds. The control member includes: a mask connection recognizing unit for recognizing whether the mask is connected or not when the control line of the mask is connected to the control line connecting unit of the controller; a care item managing unit for registering working patterns and working time of the RGB LEDs and the IR LEDs of the mask, and names of care according to purposes; a care item selection unit for providing care menus so that the user can select the registered care items through the care item managing unit; a working time setting unit for setting working time for the selected care item; and a care item operating unit for providing the mask with the control signals of the RGB LEDs and the IR LEDs of the mask to correspond to the pattern of the selected care item when the user selects the care item.

Preferably, when the end of the control line of the mask is combined to the control line connecting unit of the controller, the mask connection recognizing unit supplies minute electric currents, checks an amount of feedback currents, and recognizes the mask when a value of the feedback current and a current value of the registered mask match.

Preferably, the care item selection unit includes: a mask display unit for displaying the shape of the mask and selectable zones on the display unit so that different care items are usable on the mask at the same time; and a care zone selection unit for getting registration when the user selects and registers a wanted zone and a care item on the display unit through the mask display unit.

As described above, the mask device for facial skin care according to a preferred embodiment of the present invention can relieve facial skin troubles of various kinds using RGB LED lights and IR LED lights, protect the sight of eyes, and relieve the pressure applied to the eyes even though a user wears it for a long time.

Moreover, the mask device for facial skin care according to a preferred embodiment of the present invention can provide LEDs more than the conventional skin care devices having LEDs formed individually because the RGB LEDs are formed integrally.

Furthermore, the mask device for facial skin care according to a preferred embodiment of the present invention can do skin care at one zone or provide different skin care functions at the same time because the user can select working zones of the RGB LED and the IR LEDs.

Additionally, the mask device for facial skin care according to a preferred embodiment of the present invention can control the width of lights radiated from the RGB LEDs and the IR LED while moving the RGB LEDs and the IR LEDs.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIG. 8 is an exemplary view of RGB LEDs and IR LEDs by items for skin care;

DETAILED DESCRIPTION OF THE PREFERRED EMBODIMENT

Figure 1A:
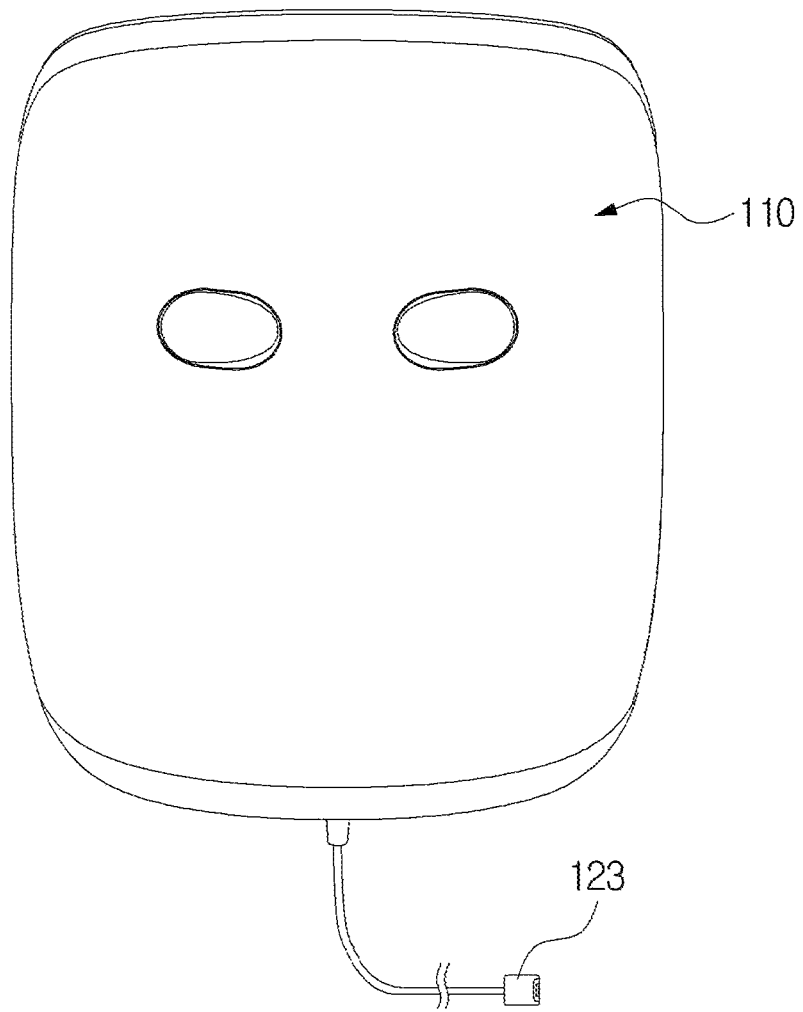
FIGS. 1A and 1B are perspective views of a mask device for facial skin care according to a preferred embodiment of the present invention.
Figure 1B:
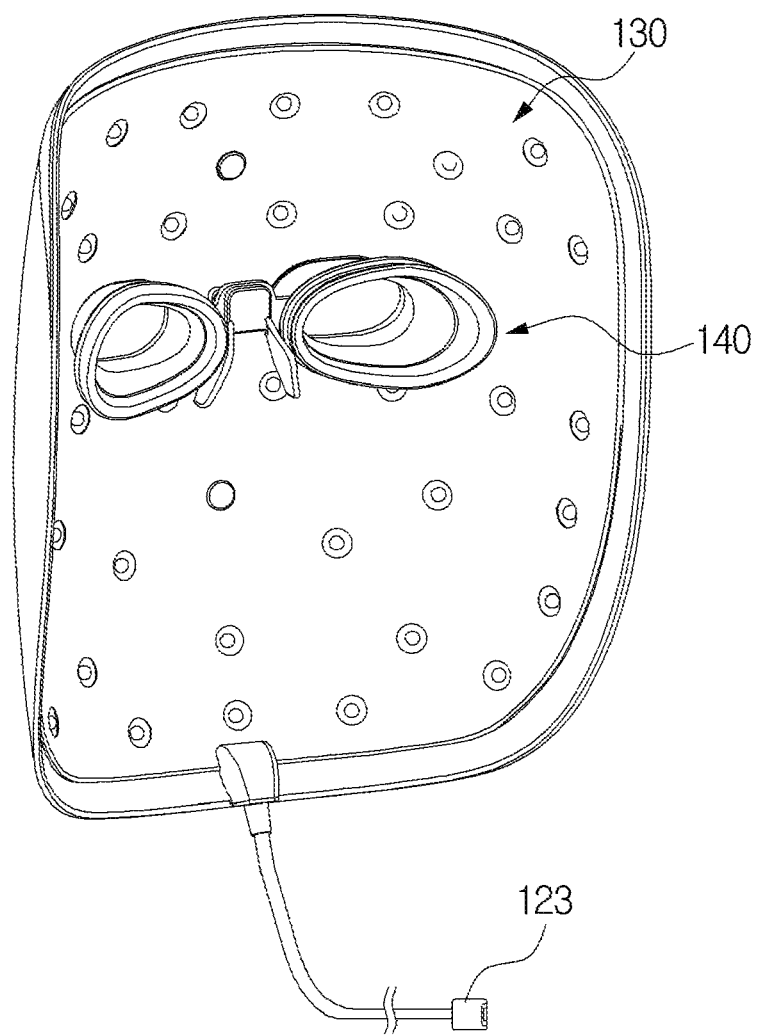

Hereinafter, exemplary embodiments of the present invention will be described with reference to the accompanying drawings.

A mask device for facial skin care according to a preferred embodiment of the present invention includes a mask 100 generating RGB lights and IR lights, and a controller 200 for providing the mask 100 with electric power and an optical control signal.

The mask 100 includes an outer mask 110, an LED module 120, an inner mask 130, and an eye protection member 140.

Figure 2:
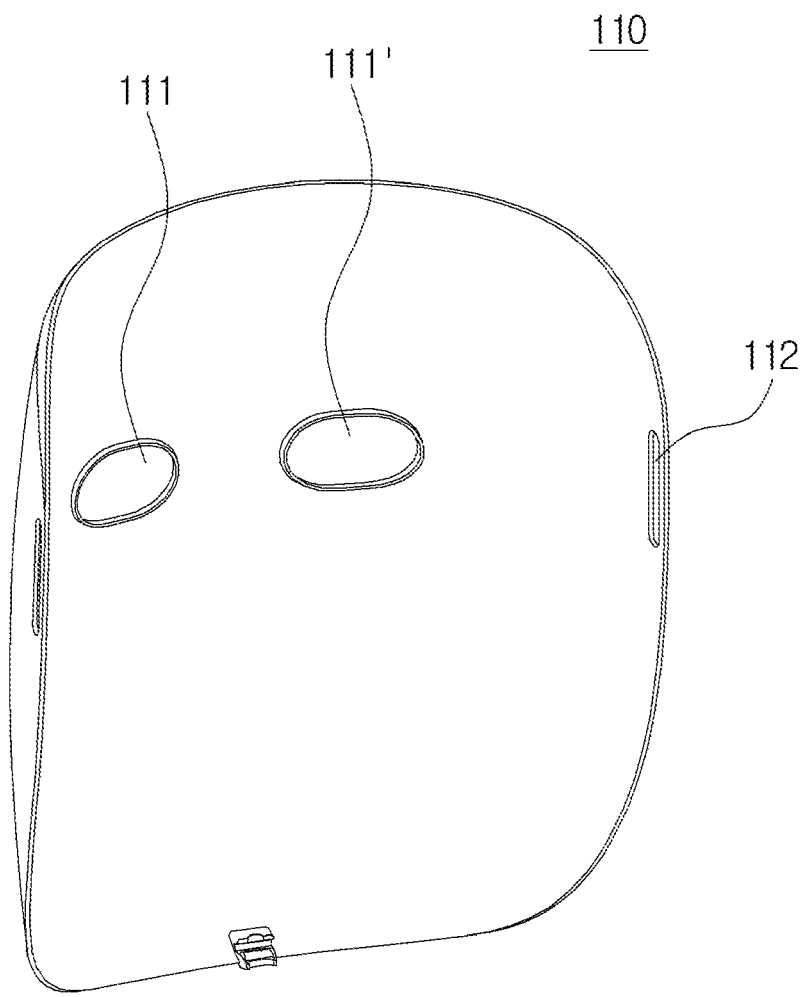
FIG. 2 is an exploded perspective view of FIG. 1.

As shown in FIG. 2, the outer mask 110 is formed to be spaced apart from a user's face at a predetermined interval and has a size to cover the whole face. The outer mask 110 has first and second eye protection holes 111 and 111' formed to be located around the user's eyes, and slots 112 formed at a left end portion and a right end portion. A wearing member 300 which allows a user to wear the mask device on his or her head is combined to the slots 112. Here, the slots 112 are elongated holes. It is preferable that the outer mask 110 be formed in a U shape to cover the user's face. It is also preferable that a through hole (not shown) be formed to be located around the user's mouth.

Figure 3:
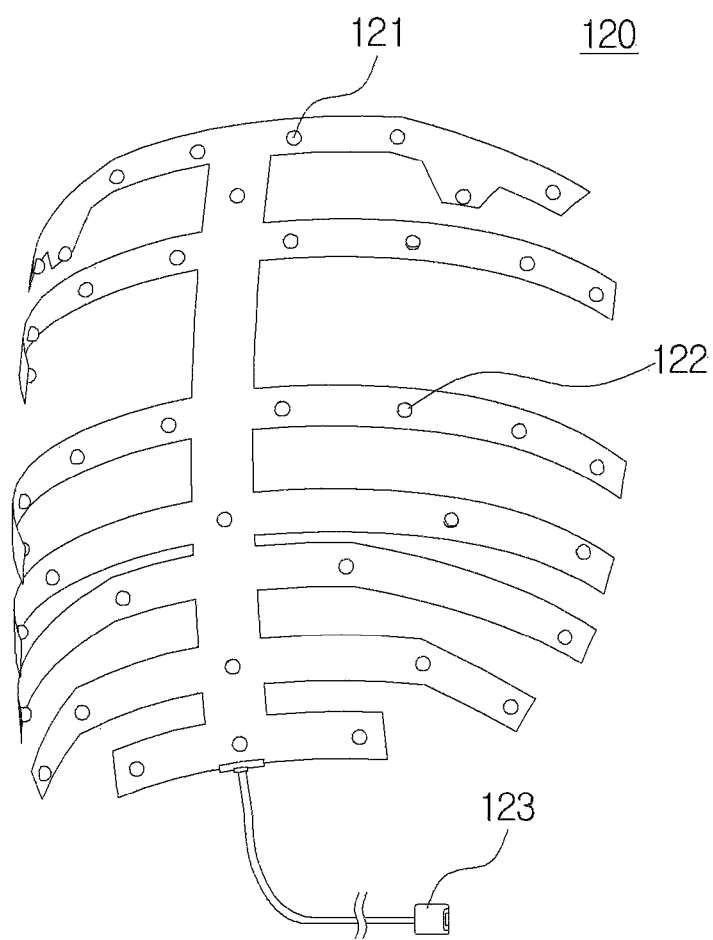
FIG. 3 is a perspective view of an outer mask according to the preferred embodiment of the present invention.

As shown in FIG. 3, the LED module 120 is located on the inner face of the outer mask 110, and has a plurality of RGB LEDs 121 for generating RGB colors, and a plurality of IR LEDs 122 for generating infrared lights. Moreover, a control line 123 which is provided with electric power and a control signal connected to an external controller 200 is connected to the LED module 120.

Figure 4:
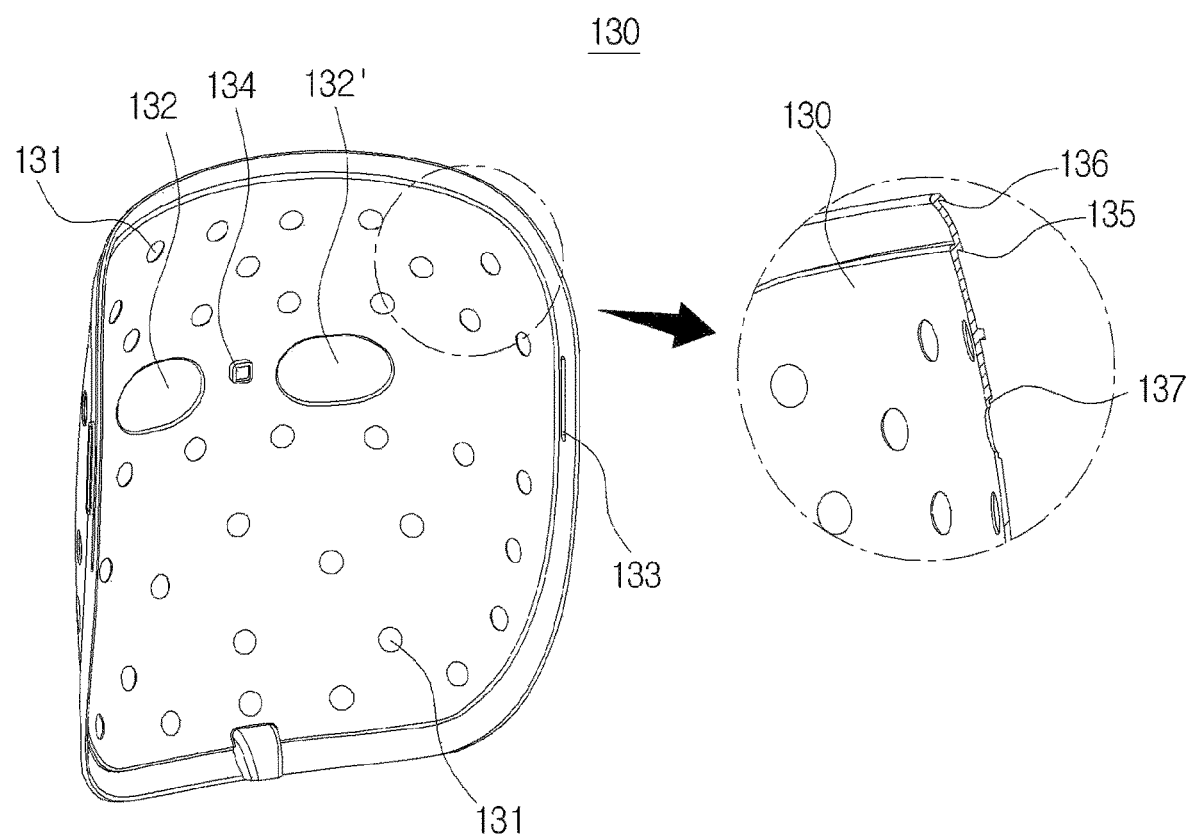
FIG. 4 is a perspective view of an inner mask according to the preferred embodiment of the present invention.

As shown in FIG. 4, the inner mask 130 is located outside the LED module 120, has a size to cover the whole face, and is joined to the outer mask 110. The inner mask 130 includes LED through holes 131 formed at portions corresponding to the LEDs, such that lights generated from the RGB LEDs 121 and the IR LEDs 122 mounted on the LED module 120 face toward the user's face. Additionally, the inner mask 130 is formed opaquely to block penetration of lights through any other portions but the LED through holes 131. Here, lights generated from the RGB LEDs 121 and the IR LEDs 122 do not penetrate through the opaque part of the inner mask 130, but may be radiated toward the user's face only through the LED through holes 131.

Moreover, the inner mask 130 includes first and second eye protection holes 132 and 132', which correspond to the first and second eye protection holes 111 and 111', and to which the eye protection member 140 is combined, and slots 133 formed at a left end portion and a right end portion so that the wearing member 300 is combined to the inner mask 130. Here, the slots 133 are elongated holes corresponding to the slots 112. Because a band or the like may be directly connected to the slots 112 and 133 in a state where one of the slots 112 and 133 is put on the other one, the mask device can be worn on the user's head without using the wearing member 300.

Furthermore, an arm type protrusion 134 may protrude between the first and second eye protection holes 132 and 132' to specify and fix the position of the eye protection member 140.

Such an inner mask 130 has a stepped portion 135 formed at an edge portion so that the inside part on which the LED module 120 is located is spaced apart from the outer mask 110 at a predetermined interval. That is, when the edge portion gets in contact with the outer mask 110, the inside part of the inner mask 130 is spaced apart from the outer mask 110 such that a space for movement of the LED module 120 is formed. In addition, preferably, an end 136 of the inner mask 130 protrudes toward the outer mask 110, so as to prevent an accident caused by exposure of an end portion of the outer mask 110 when the inner mask 130 is combined with the outer mask 110. In this instance, in the case that the outer mask 110 has a mouth protection hole formed at a portion corresponding to the user's mouth, the inner mask 130 also has a mouth protection hole. Moreover, the inner mask 130 further includes stepped jaws 137 respectively formed on the outer peripheral surfaces of the through holes to surround and hold the LEDs of the LED module 120.

Figure 5:
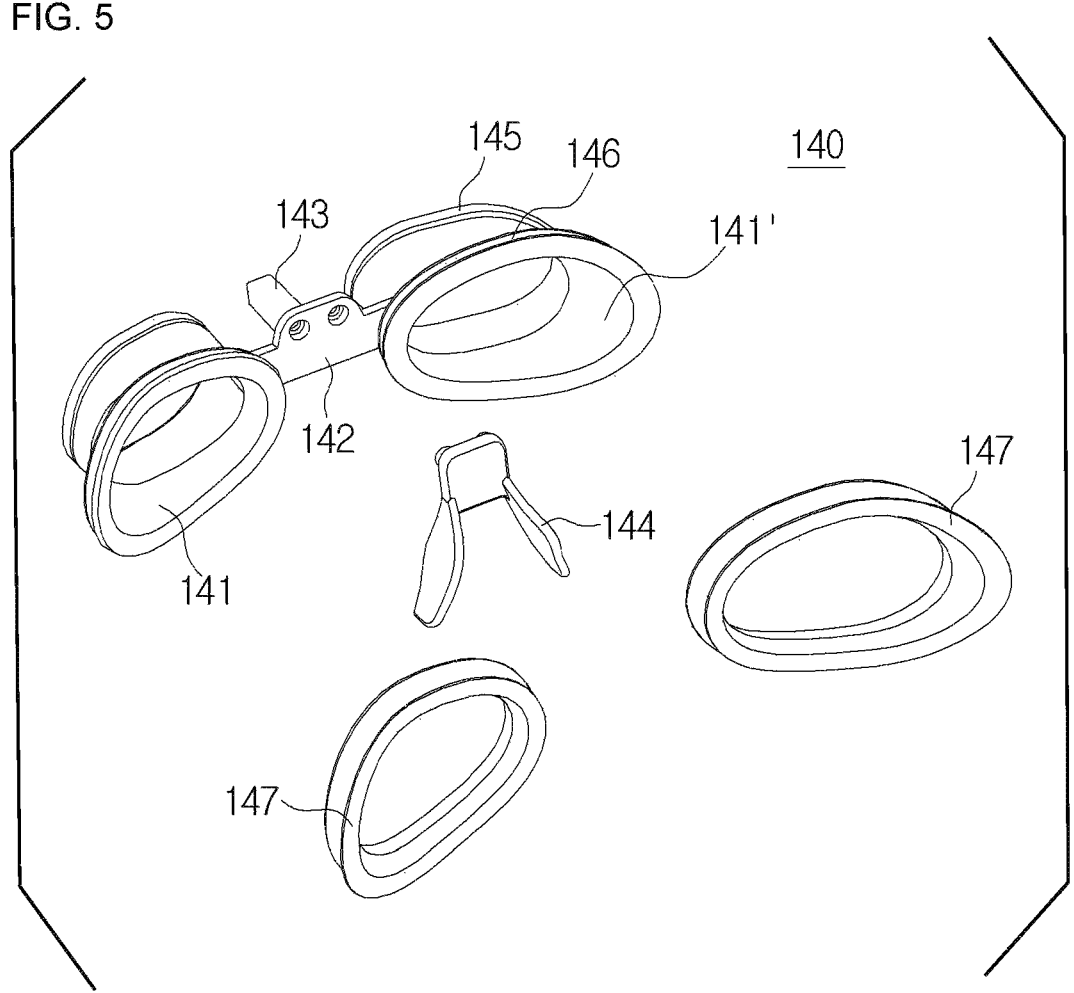
FIG. 5 is an exploded perspective view of an eye protection member according to the preferred embodiment of the present invention.

As shown in FIG. 5, the eye protection member 140 has an end combined to the first and second eye protection holes 132 and 132' of the inner mask 130 and the other end protruding to come into contact with the user's eye. Such an eye protection member 140 includes: first and second protection tubes 141 and 141' which are in a cylindrical form and of which end portions are respectively combined to the first eye protection hole 132 and the second eye protection hole 132'; a connector 142 of which one end and the other end are respectively combined to the first and second protection tubes 141 and 141' to support the first and second protection tubes 141 and 141'; a fixing rod 143 which extends from the central lower portion of the connector 142 and is combined to the arm type protrusion 134 of the inner mask 130; and a nose support 144 which extends from the fixing rod 143 to be put on the user's bridge of the nose. Furthermore, stoppers 145 are respectively formed on the first and second protection tubes 141 and 141' combined to the first and second eye protection holes 132 and 132' to protrude outwardly. Such stoppers 145 prevent the first and second protection tubes 141 and 141' from being separated from the first and second eye protection holes 132 and 132' after the ends of the first and second protection tubes 141 and 141' are respectively inserted into the first and second eye protection holes 132 and 132'.

Additionally, the eye protection member 140 has insertion grooves 146 respectively formed in the outer faces of the first and second protection tubes 141 and 141', and protection covers 147 respectively combined to the insertion grooves 146 while surrounding the first and second protection tubes 141 and 141'. The mask device for facial skin care according to the preferred embodiment of the present invention can prevent injuries due to the protection cover 147 even though the user's eyes come into contact with the eye protection member 140 and maintain comfortability.

Figure 6:
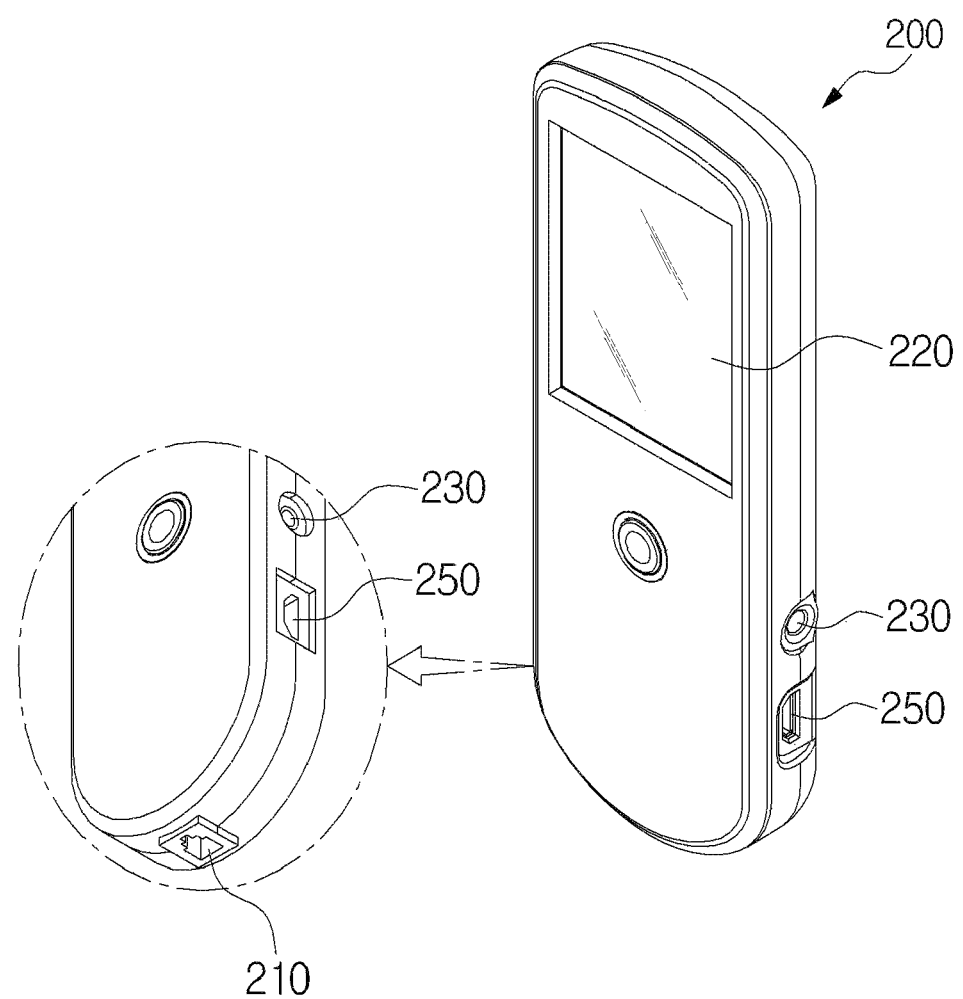
FIG. 6 is a perspective view of a controller according to the preferred embodiment of the present invention.

In the meantime, as shown in FIG. 6, the controller 200 includes: a control line connecting unit 210 to which the control line 123 of the mask is connected; a display unit 220 for displaying information of various menus; an earphone connecting unit 230 to which an earphone is inserted; a battery (not shown) for supplying electric power to the mask and the controller; and a control member 240 for controlling information of various kinds. In this instance, preferably, the battery is a lithium polymer battery usable for a long time, and is charged by receiving electric power from the outside through a power connection unit 250 located at one side. In this instance, if the lithium polymer battery is used, the mask device can be used for a long time on a single charge.

Figure 7:
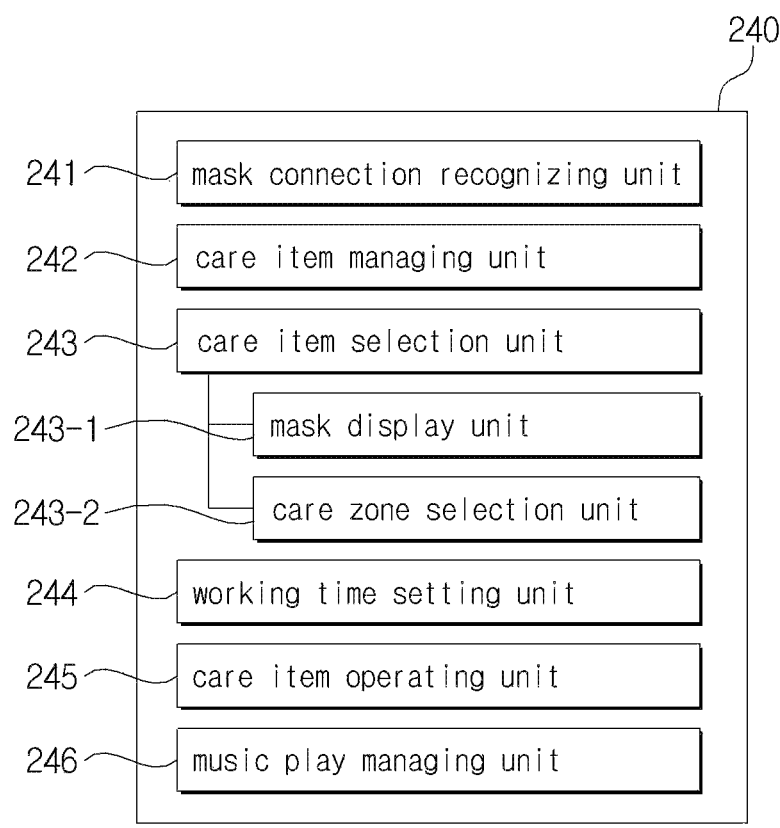
FIG. 7 is a block diagram of a control member according to the preferred embodiment of the present invention.
Figure 9:
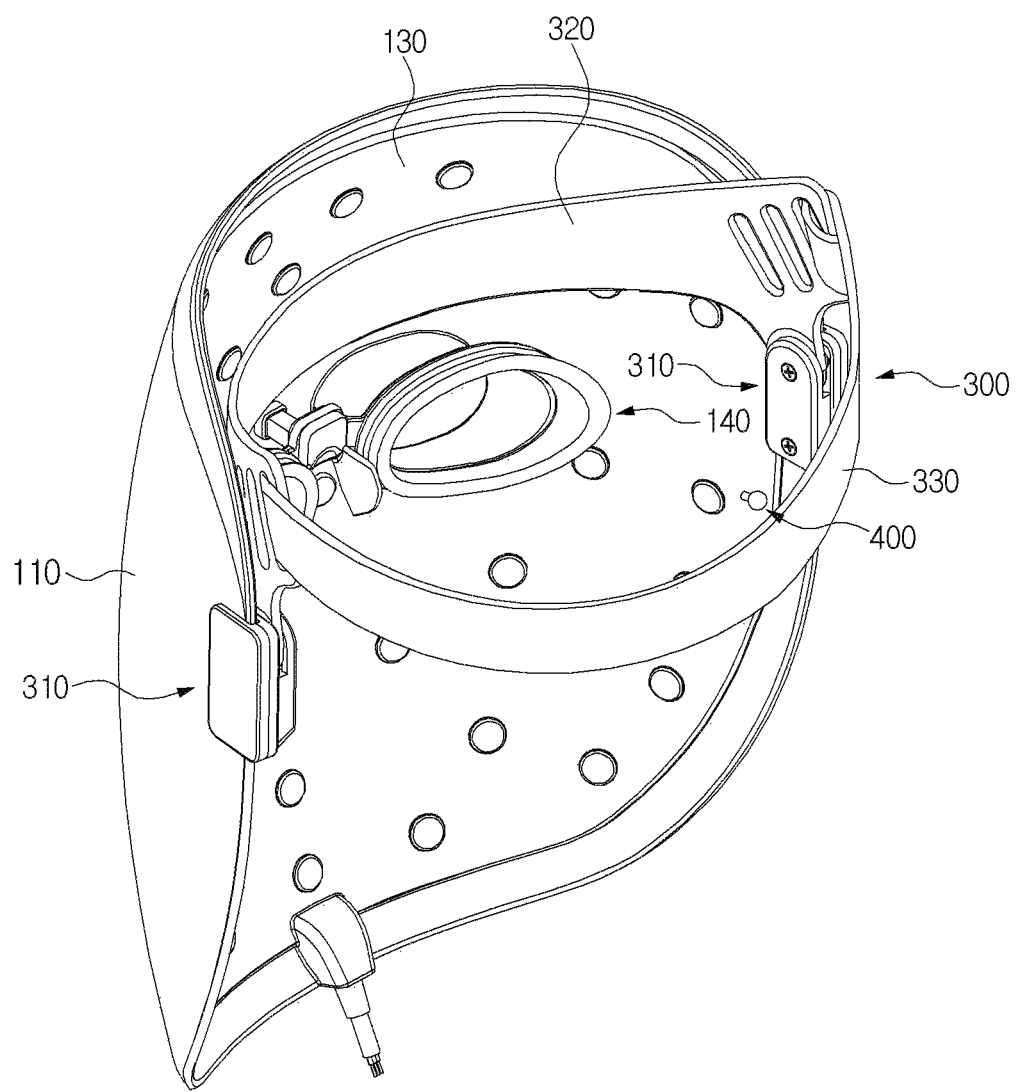
FIG. 9 is a perspective view of a mask device for facial skin care according to another preferred embodiment of the present invention.

As shown in FIG. 7, the control member 240 includes a mask connection recognizing unit 241, a care item managing unit 242, a care item selection unit 243, a working time setting unit 244, a care item operating unit 245, and may further include a music play managing unit 246.

The mask connection recognizing unit 241 recognizes whether the mask 100 is connected or not when the control line 123 of the mask 100 is connected to the control line connecting unit 210. When an end of the control line 123 of the mask 100 is combined to the control line connecting unit 210 of the controller 200, the mask connection recognizing unit 241 supplies minute electric currents, checks an amount of feedback currents, and recognizes the mask 100 when a value of the feedback current and a current value of the registered mask 100 match.

The care item managing unit 242 registers working patterns and working time of the RGB LEDs 121 and the IR LEDs 122 of the mask 100, and names of care according to care purposes. Preferably, such care items are received through wire and wireless networks to be registered. For instance, as shown in FIG. 8, the care items contains therapy items, such as pimple, scar, atopy, psoriasis, and injuries, healing items, such as relaxing effect, prevention of infection, skin refreshing, and pain relief, tightening items, such as wrinkle treatment, prevention of hair loss, cellulite treatment, and promotion of blood circulation, and beauty items, such as sedation of skin troubles, resistance to ultraviolet rays, generation of collagen, and inhibition of sebum, and different colors are registered according to the care items.

The care item selection unit 243 provides care menus so that the user can select care items registered through the care item managing unit 242. Preferably, the care item selection unit 243 includes a mask display unit 243-1, and a care zone selection unit 243-2.

The mask display unit 243-1 displays the shape of the mask 100 and selectable zones of the right, left, top and bottom on the display unit 220 so that the user can simultaneously use different care items of the mask 100.

The care zone selection unit 243-2 gets registration when the user selects and registers a zone to be treated on the shape of the mask 100 and a care item on the display unit 220 through the mask display unit 243-1. So, the user can select and register care items by zones, such as the forehead part, the right cheek part, the left cheek part, and the chin part, by the care zone selection unit 243-2.

The user sets working time for the selected care item using the working time setting unit 244. The working time setting unit 244 has a default working time set previously for care items, and the user can control setting time when a display screen is shown for allowing the user's selection. For instance, the default working time is set to 20 minutes, but the user can control the setting time to 5 minutes, 10 minutes, 20 minutes and others.

The care item operating unit 245 provides the mask 100 with a control signal of the RGB LEDs 121 and the IR LEDs 122 of the mask 100 to correspond to the set pattern of the selected care item when the user selects a care item. The control signal of the care item operating unit 245 is provided to the LED module 120 through the control line 123 of the mask 100, so that the RGB LEDs 121 and the IR LEDs 122 light up in color patterns according to the control signal to emit lights.

The music play managing unit 246 provides an MP3 function such that the user can listen to music while wearing the mask 100. The music play managing unit 246 displays menus related with music play on the display unit 220, and provides music through a speaker or an earphone when the user selects music.

Hereinafter, an operational process of the mask device for facial skin care according to the preferred embodiment of the present invention will be described.

First, the user wears the mask 100 in order to care the face skin. In this instance, the eye protection member 140 combined to the inner mask 130 gets in contact with the user's eyes, so that it can prevent that LED lights emitted through the LED holes 131 of the inner mask 130 from being directly radiated to the user's eyes.

Moreover, in the state where the user wears the mask 100, when the user connects the control line 123 connected to the LED module 120 of the mask 100 to a mask connector of the controller 200, the controller 200 checks whether the mask 100 is connected or not. That is, when the end of the control line 123 of the mask 100 is combined to the control line connecting unit 210 of the controller 200, the mask connection recognizing unit 241 supplies minute electric currents, checks an amount of feedback currents, and recognizes the mask 100 when the value of the feedback current and the current value of the registered mask 100 match.

After that, the user selects one of the registered care menus using the care item selection unit 243 of the controller 200. In this instance, if the user wants to treat only a part of the face, the user can select a mask shape, one of the zones of the right, left, top and bottom, and one of the care items displayed on the display unit 220 of the controller 200. Moreover, the working time for the selected care item is set in default, but the user can control the working time by 5 minutes, 10 minutes, 20 minutes, and others.

Through the above process, when a care menu is selected, the care item operating unit 245 of the controller 200 supplies the control signal of the RGB LEDs 121 and the IR LEDs 122 of the mask 100 to the mask 100 so as to correspond to the set color pattern of the selected care item. The control signal of the care item operating unit 245 is supplied to the LED module 120 through the control line 123 of the mask 100, such that the RGB LEDs 121 and the IR LEDs 122 are lit in the pattern according to the control signal to emit lights. As described above, when the care menu is operated, working LEDs and remaining working time are displayed on the display unit 220 of the controller 200 so that the user can check them.

Additionally, when the working time expires, electric power supplied to the control line 123 of the mask 100 is shut off, and the mask 100 stops operation.

In the meantime, the user can listen to music through a speaker or an earphone by activating the MP3 function while wearing the mask 100.

Moreover, as shown in FIGS. 9 to 12, the mask device for facial skin care according to the preferred embodiment of the present invention includes the wearing member 300 which is worn on the user's head in the state where the outer mask 110 and the inner mask 130 are combined and fixed.

Figure 10:
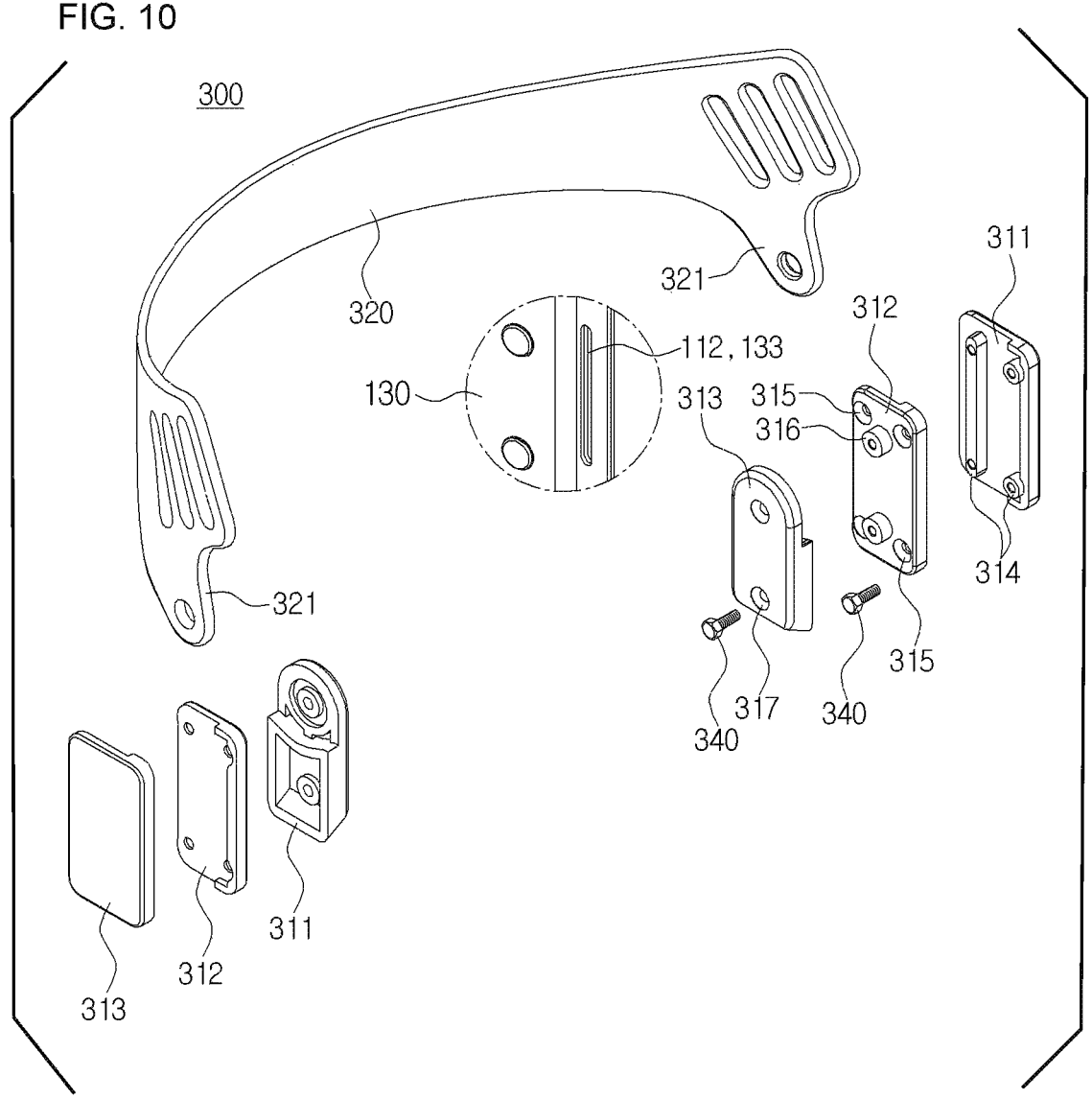
FIG. 10 is a perspective view of a wearing member applied to FIG. 9.

As shown in FIG. 10, the wearing member 300 includes: fixing blocks 310 fixed at both sides of the outer mask 110 and the inner mask 130; a forehead holder 320 rotatably fixed on the fixing blocks 310 to support the user's forehead; an occipital region holder 330 disposed on the forehead holder 320 to support the user's occipital region; and fastening members 340 which penetrate the fixing blocks 310, the forehead holder 320, the slots 112 of the outer mask 110, and the slots 133 of the inner mask 130 to fix the fixing blocks 310 to the outer mask 110 and the inner mask 130 and support rotation of the forehead holder 320.

Each of the fixing blocks 310 includes an outer block 311 located at the outer mask 110, an inner block 312 located at the inner mask 130 to be combined to the outer block 311, and a support block 313 combined to the inner block 312 to support the forehead holder 320.

The outer block 311 has a plurality of outer fastening portions 314 to which the fastening member 340 is combined. One of the outer fastening portions 314 may be formed in a rectangular shape to correspond to the slots 112 and 133 which are elongated holes. The outer fastening portions 314 and inner fastening portions 316 may respectively have screw taps to which the fastening members 340 of a blot type are screw-coupled. The outer block 311 may provide an esthetic sense of a simple appearance because the outer fastening portions 314 are formed on one side and the other side is formed flat. Here, when the outer fastening portions 314 of the rectangular shape are inserted and fixed into the elongated slots 112 and 133, the outer block 311 may be kept firmly on the mask 100 without being rotated.

The inner block 312 has a plurality fastening holes 315, which correspond to the outer fastening portions 314 and through which the fastening member 340 penetrates, and a plurality of inner fastening portions 316 corresponding to the support block 313 are formed on the inner block 312. The inner fastening portions 316 respectively have screw taps to which the fastening members 340 of a bolt type are screw-coupled.

The support block 313 has a plurality of fastening holes 317 which correspond to the inner fastening portions 316 and through which the fastening members 340 penetrate.

The forehead holder 320 is made with a flexible plate which is bent in the form of an arc, and both ends of the forehead holder 320 are fixed to the fixing block 310 by the fastening members 340. Such a forehead holder 320 may generally get in contact with the user's forehead while being bent. Furthermore, the forehead holder 320 may have projections 321, which project downwardly from both sides thereof and through which the fastening members 340 penetrate. Therefore, when the projections 321 rotate at the fixing blocks 310, the forehead holder 320 can rotate without interference of the fixing blocks 310.

The occipital region holder 330 may be a band fixed at both ends of the forehead holder 320. The occipital region holder 330 is elastically supported on the user's occipital region to prevent the forehead holder 320 from being separated from the user's forehead.

The fastening members 340 may be a plurality of bolts, and are fastened to the outer fastening portions 314 inserted into the slots 112 and 133 after penetrating the fastening holes 315, so as to fix the outer block 311 and the inner block 312 to be pressed to the outer mask 110 and the inner mask 130. After that, the fastening members 340 passes through the forehead holder 320 while penetrating the fastening holes 317, are fastened to the inner fastening portions 316, and then, rotatably fix the forehead holder 320 while fastening the inner block 312 and the support block 313. That is, the bolts of the fastening members 340 are screw-coupled to the screw taps of the outer fastening portions 314 and the inner fastening portions 316. In this instance, a screw thread is not formed at the central portion where the forehead holder 320 is supported but is formed only at the outer face of an end portion thereof, so as to prevent abrasion of the projections 321 of the forehead holder 320 by the screw thread.

Moreover, because a plurality of the fastening members 340 respectively pass through the fastening holes 312 and are fastened after respectively penetrating both sides of the elongated slots 112 and 133, the fixing block 310 can be kept firmly in a fixed state without being rotated on the mask 100.

Figure 11:
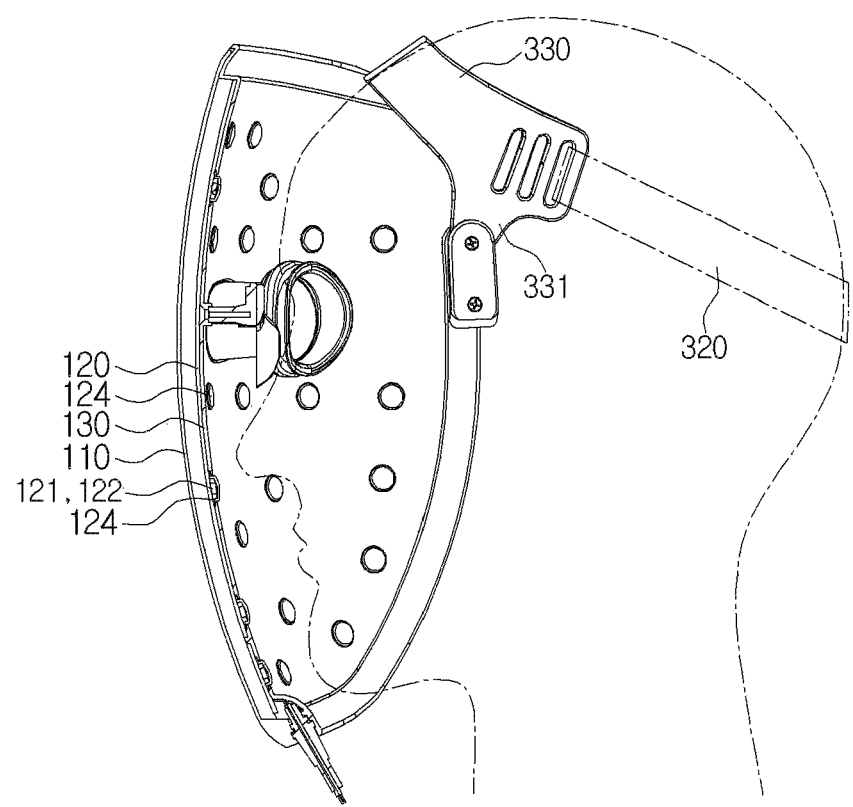
FIG. 11 is a view showing a state where the wearing member is worn on a person with a small head.
Figure 12:
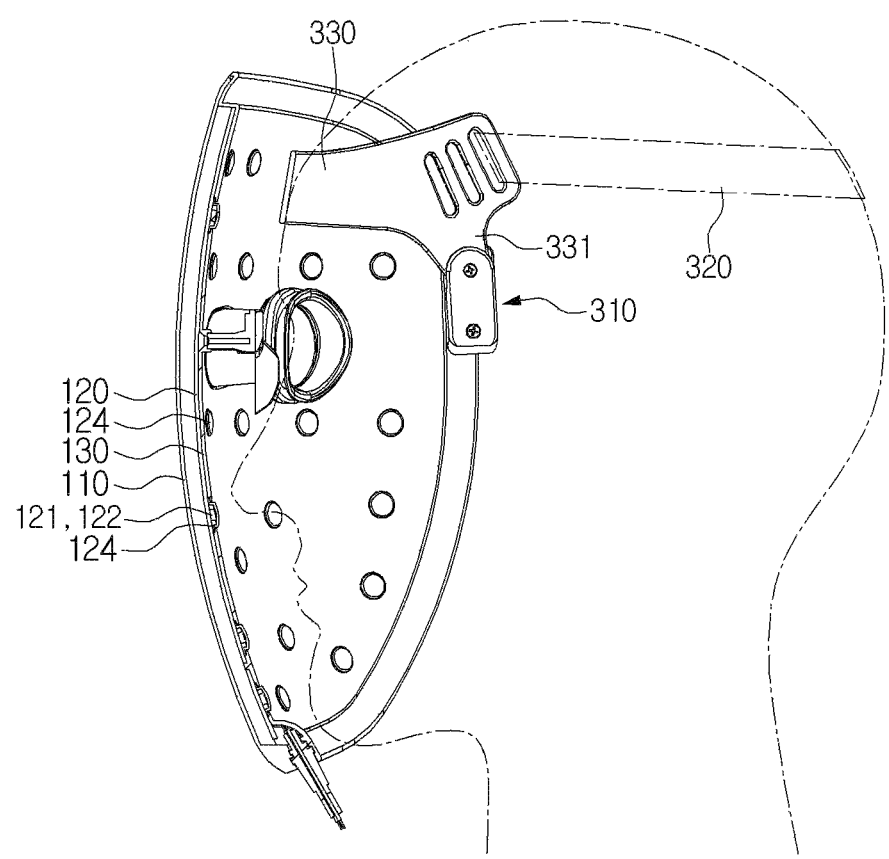
FIG. 12 is a view showing a state where the wearing member is worn on a person with a big head.

As shown in FIGS. 11 and 12, because the forehead holder 320 of the wearing member 300 is bent and rotated in the form of an arc around the end portion, in the case of a user with a small head, the forehead holder 320 may be put on the upper part of the user's head, or in the case of a user with a big head, the forehead holder 320 may be supported on the forehead of the user's head. As described above, because the forehead holder 320 is supported regardless of the size of the user's head, the mask device can relieve pressure applied to the eyes even though users with different head sizes wear it for a long time.

Figure 13:
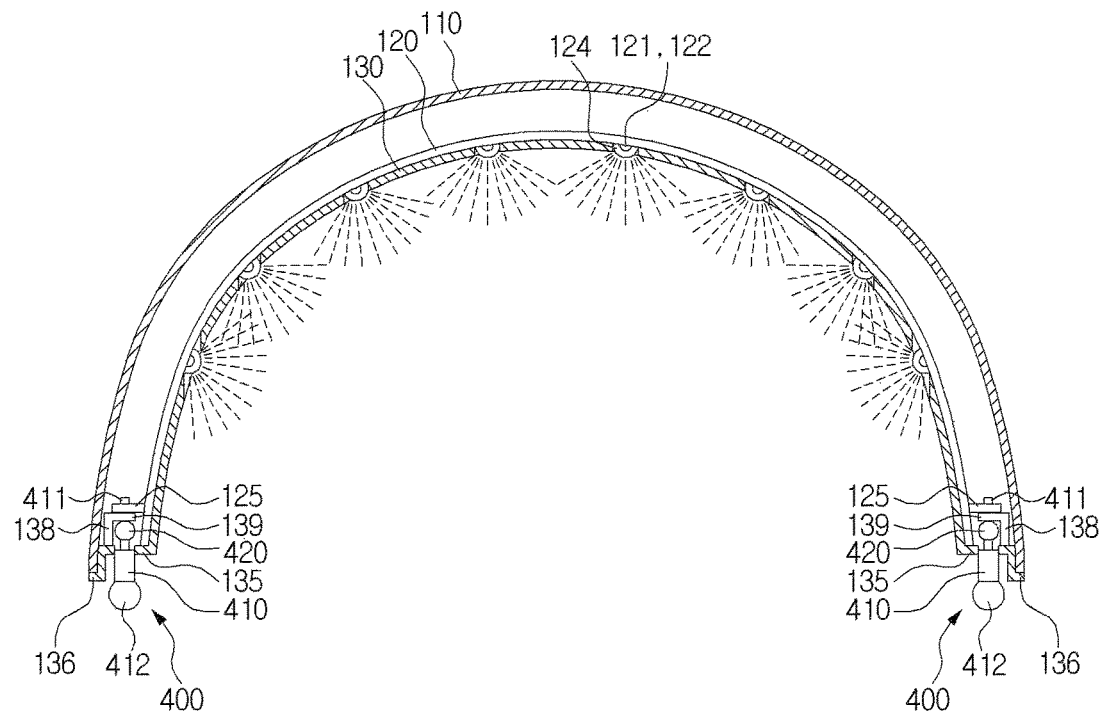
FIG. 13 is a sectional view of a mask device for facial skin care according to a further preferred embodiment of the present invention.
Figure 16:
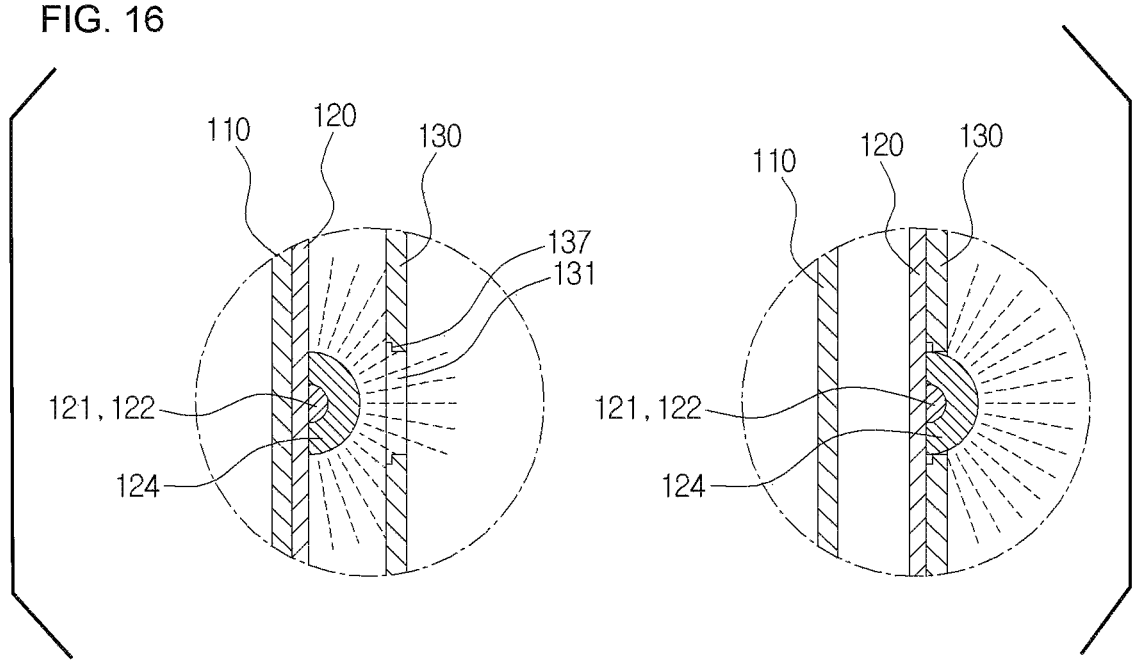
FIG. 16 is a partially sectional view showing a light diffusion member applied to FIG. 13.

Furthermore, as shown in FIGS. 13 and 16A and 16B, the mask device for facial skin care according to the present invention includes light diffusion members 124, which are respectively disposed on the RGB LEDs 121 and the IR LEDs 122 to diffuse emitted lights. The light diffusion members 124 are formed in a convex shape like a transparent convex lens and are disposed on the LED module 120 to respectively cover the RGB LEDs 121 and the IR LEDs 122 so as to diffuse lights emitted from the RGB LEDs 121 and the IR LEDs 122. Namely, the diffused lights may be evenly provided to the face of the user who is wearing the mask 100.

Figure 14:
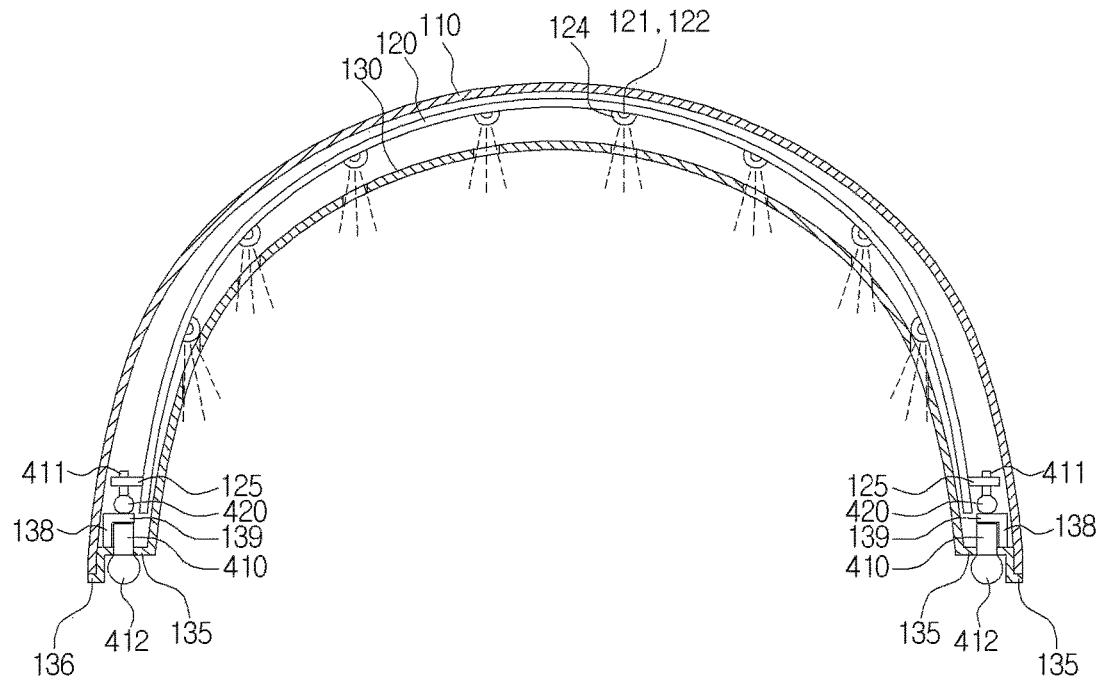
FIG. 14 is a sectional view showing a state where an LED module is moved from FIG. 13.
Figure 15:
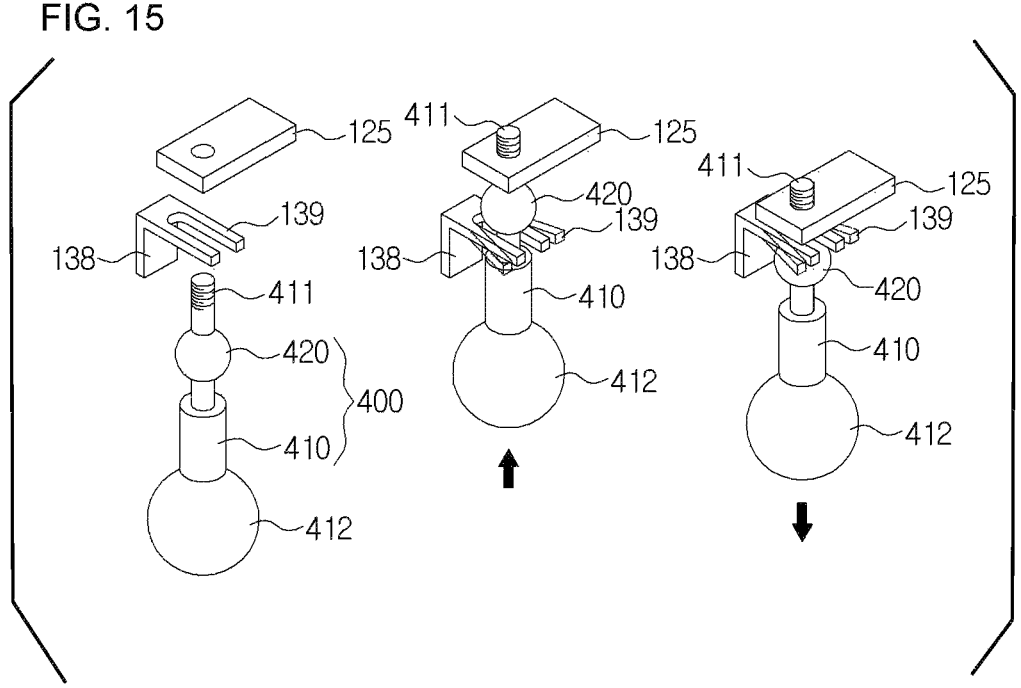
FIG. 15 is a view showing an operational state of an LED module interval control member applied to FIG. 13.

Additionally, as shown in FIGS. 13 and 14, a bracket 138 is formed at the stepped portion 135 formed on the inner mask 130. The bracket 138 has a yoke 139 transformed elastically.

As shown in FIGS. 13 to 16B, the mask device for facial skin care according to the present invention includes an LED module interval control member 400, which is movably supported on the bracket 138 to pull the LED module 120 so that the LED module 120 gets in contact with the inner mask 130, or to push the LED module 120 so that the LED module 120 is spaced apart from the inner mask 130.

The LED module interval control member 400 includes: a shaft 410 whose one end is fixed to the LED module 120 and the other end protrudes outwardly after penetrating the inner mask 130 and which is guided through the yoke 139 of the bracket 138; and a fixing protrusion 420 which is formed on the shaft 410 and is movably caught and fixed to the yoke 139 of the bracket 138.

The shaft 410 is formed in a cylindrical shape, and the fixing protrusion 420 is formed in a spherical shape at the middle portion of the shaft 410. The spherical fixing protrusion 420 must be larger in diameter than the shaft 410.

Therefore, when the user pulls the shaft 410 outwardly or pushes the shaft 410 inwardly in the state where the user grasps the mask 100, the fixing protrusion 420 forcedly penetrates the yoke 139 of the bracket 138, and then, is caught and supported to the yoke 139 of the bracket 138. Here, when the user pulls the shaft 410 outwardly, because the fixing protrusion 420 is caught and supported to one side of the yoke 139 after forcedly penetrating the yoke 139 of the bracket 138, the LED module 120 is pulled and gets in contact with the inner mask 130. On the contrary, when the user pushes the shaft 410 inwardly, because the fixing protrusion 420 is caught and supported to the other side of the yoke 139 after forcedly penetrating the yoke 139 of the bracket 138, the LED module 120 is pushed to be spaced apart from the inner mask 130.

As described above, when the LED module 120 is spaced apart from the inner mask 130, because the RGB LEDs 121 and the IR LEDs 122 of the LED module 120 are separated from the LED holes 131, lights emitted from the RGB LEDs 121 and the IR LEDs 122 are radiated as much as the size of the LED holes 131 even though the lights are diffused through the light diffusion member 124. That is, lights may be provided to the user's skin at a narrow irradiation angle.

On the contrary to this, when the LED module 120 gets in contact with the inner mask 130, because the RGB LEDs 121 and the IR LEDs 122 of the LED module 120 are inserted into the LED holes 131, lights diffused from the RGB LEDs 121 and the IR LEDs 122 are irradiated to be wider than the size of the LED holes 131 while being diffused through the light diffusion member 124. That is, lights diffused through the light diffusion member 124 may be provided to the user's skin at a wide irradiation angle while being diffused to the maximum without any interference to the inner circumferential surfaces of the LED holes 131.

Meanwhile, the shaft 410 may have a male screw thread 411 formed on the outer circumferential surface of an end thereof. The shaft 410 may have a hand grip 412 formed at the other end so as to allow the user to manipulate the shaft with his or her hand.

The LED module 120 may have a wing piece 125 having a screw tap corresponding to the male screw thread 411 of the shaft 410.

Therefore, when the user rotates the shaft 410 in a state where the end of the shaft 410 coincides with the screw tap of the wing piece 125, the male screw thread 411 of the shaft 410 is screw-coupled to the screw tap of the wing piece 125.

As described above, the shaft 410 can be conveniently combined to the LED module 120 or separated from the LED module 120 by the male screw thread 411 formed on the shaft 410 and the wing piece 125 having the screw tap.

As described above, while the present invention has been particularly shown and described with reference to the exemplary embodiment thereof, it will be understood by those of ordinary skill in the art that the protective scope of the present invention is not limited to the above embodiment and various changes, modifications and equivalences may be made therein without departing from the technical idea of the present invention.

What is claimed is:

1. A mask device for facial skin care, which includes a mask generating RGB lights and IR lights, and a controller for providing the mask with electric power and optical control signals, wherein the mask comprises:
an outer mask, which is formed to be spaced apart from a user's face at a predetermined interval, has a size to cover the whole face, and includes first and second eye protection holes located around the eyes and slots respectively formed at a left end portion and a right end portion;

an LED module, which is located on the inner face of the outer mask and includes a plurality of RGB LEDs for generating RGB colors and a plurality of IR LEDs for generating infrared rays, and to which a control line receiving electric power connected to the an external controller of the outside and for receiving electric power and a control signal is connected;

an inner mask, which is located outside the LED module, has a size to cover the whole face, is combined to the outer mask, includes LED through holes formed corresponding to the LEDs so that lights generated from the RGB LEDs and the IR LEDs of the LED module face toward the user's face, is formed opaquely to block penetration of lights through any other portions but the LED through holes, and includes first and second eye protection holes formed to correspond to the first and second eye protection holes of the outer mask and slots respectively formed at the left end portion and the right end portion;

an eye protection member whose one end is combined to the first and second eye protection holes of the inner mask and the other end protrudes to come into contact with the user's eyes;

light diffusion members of a convex form respectively disposed on the RGB LEDs and the IR LEDs to diffuse emitted lights; and a wearing member fixed to combine the outer mask and the inner mask with each other and worn on the user's head, wherein the wearing member comprises:
fixing blocks fixed at both sides of the outer mask and the inner mask;
a forehead holder rotatably fixed on the fixing block and supported on the user's forehead;
an occipital region holder disposed on the forehead holder to be supported on the user's occipital region; and
fastening members which penetrate the fixing blocks, the forehead holder, the slots of the outer mask, and the slots of the inner mask to fix the fixing blocks to the outer mask and the inner mask and support rotation of the forehead holder, wherein the inner mask has a stepped portion, which has a bracket and is formed at an edge portion so that the inside part on which the LED module is located is spaced apart from the outer mask at a predetermined interval, and wherein an LED module interval control member is movably supported on the bracket to pull the LED module so that the LED module gets in contact with the inner mask, or to push the LED module so that the LED module is spaced apart from the inner mask.

2. The mask device according to claim 1, wherein an arm type protrusion is formed to protrude between the first and second eye protection holes to fix the position of the eye protection member, wherein stepped jaws are respectively formed on the outer circumferential surfaces of the LED through holes of the inner mask to surround and support the LEDs of the LED module, wherein the eye protection member comprises: first and second protection tubes which are in a cylindrical form and of which end portions are respectively combined to the first eye protection hole and the second eye protection hole; a connector of which one end and the other end are respectively combined to the first and second protection tubes; a fixing rod which extends from the central lower portion of the connector and is combined to the arm type protrusion of the inner mask; a nose support which extends from the fixing rod to be put on the user's bridge of the nose; insertion grooves respectively formed in the outer faces of the first and second protection tubes; and protection covers respectively combined to the insertion grooves while surrounding the first and second protection tubes; and wherein stoppers are respectively formed on the first and second protection tubes inserted into the inner mask to protrude outwardly in order to prevent the first and second protection tubes from being separated from the first and second eye protection holes after the ends of the first and second protection tubes are respectively inserted into the first and second eye protection holes.

3. The mask device according to claim 1, wherein the fixing block comprises:

an outer block located at the outer mask;

an inner block located at the inner mask to be combined to the outer block; and a support block combined to the inner block to support the forehead holder, wherein the outer block has a plurality of outer fastening portions to which the fastening member is combined, the inner block has a plurality fastening holes, which correspond to the outer fastening portions and through which the fastening member penetrates, and a plurality of inner fastening portions corresponding to the support block, and the support block has a plurality of fastening holes which correspond to the inner fastening portions and through which the fastening members penetrate, and wherein a plurality of fastening members are combined to the outer fastening portions inserted into the slots after passing through the fastening holes so as to be fixed while pressurizing the outer block and the inner block to the outer mask and the inner mask, is combined to the inner fastening portions after passing through the forehead holder while penetrating the fastening holes, such that the inner block and the support block are combined and the forehead holder is fixed to be able to rotate.

4. The mask device according to claim 3, wherein the slots are elongated holes, the outer fastening portions are formed in a rectangular shape to correspond to the slots, and wherein the fastening members are bolts, and the outer fastening portions and the inner fastening portions respectively have screw taps with which the bolts of the fastening members are screw-coupled.

5. The mask device according to claim 4, wherein the forehead holder is made with a flexible plate which is bent in the form of an arc, and both ends of the forehead holder are fixed to the fixing block, and wherein the occipital region holders are bands respectively fixed to both ends of the forehead holder.

6. The mask device according to claim 5, wherein the forehead holder has projections, which are formed to project downwardly form both sides there, and which are rotatably fixed to the fixing block when the fastening members penetrate therethrough.

7. The mask device according to claim 1, wherein the bracket has a yoke transformed elastically, and wherein the LED module interval control member comprises:

a shaft whose one end is fixed to the LED module and the other end protrudes outwardly after penetrating the inner mask and which is guided through the yoke of the bracket; and a fixing protrusion which is formed on the shaft and is movably caught and fixed to the yoke of the bracket.

8. The mask device according to claim 7, wherein the shaft has a male screw thread formed on the outer circumferential surface of an end thereof, and the LED module has a wing piece having a screw tap corresponding to the male screw thread of the shaft.

9. The mask device according to claim 1, wherein the controller comprises:

a control line a control line connecting unit to which the control line of the mask is connected; a display unit for displaying information of various menus; and a control member 240 for controlling information of various kinds, and wherein the control member comprises:

a mask connection recognizing unit for recognizing whether the mask is connected or not when the control line of the mask is connected to the control line connecting unit of the controller;

a care item managing unit for registering working patterns and working time of the RGB LEDs and the IR LEDs of the mask, and names of care according to purposes;

a care item selection unit for providing care menus so that the user can select the registered care items through the care item managing unit;

a working time setting unit for setting working time for the selected care item; and a care item operating unit for providing the mask with the control signals of the RGB LEDs and the IR LEDs of the mask to correspond to the pattern of the selected care item when the user selects the care item.

10. The mask device according to claim 9, wherein when the end of the 8control line of the mask is combined to the control line connecting unit of the controller, the mask connection recognizing unit supplies minute electric currents, checks an amount of feedback currents, and recognizes the mask when a value of the feedback current and a current value of the registered mask match.

11. The mask device according to claim 10, wherein the care item selection unit comprises:

a mask display unit for displaying the shape of the mask and selectable zones on the display unit so that different care items are usable on the mask at the same time; and a care zone selection unit for getting registration when the user selects and registers a wanted zone and a care item on the display unit through the mask display unit.

\* \* \* \* \*